United States Patent

Sasaoka et al.

Patent Number: 6,063,918
Date of Patent: May 16, 2000

[54] PROCESS FOR PREPARING 2-ISOCEPHEM DERIVATIVES

[75] Inventors: Michio Sasaoka; Daisuke Suzuki; Delsoo Suh; Yoshihisa Tokumaru, all of Tokushima, Japan

[73] Assignee: Otsuka Kagaku Kabushiki Kaisha, Osaka-fu, Japan

[21] Appl. No.: 08/889,048

[22] Filed: Jul. 7, 1997

Related U.S. Application Data

[62] Division of application No. 08/732,446, filed as application No. PCT/JP96/00538, Mar. 6, 1996, Pat. No. 5,688,942.

[30] Foreign Application Priority Data

Mar. 10, 1995 [JP] Japan ........................ 7-79491

[51] Int. Cl.$^7$ ........................ C07D 513/04; C07D 507/08
[52] U.S. Cl. ........................ 540/300; 540/214
[58] Field of Search ........................ 540/300

[56] References Cited

U.S. PATENT DOCUMENTS 4,831,026 5/1989 Fujii ........................ 540/300

FOREIGN PATENT DOCUMENTS 63-211283 9/1988 Japan .

Primary Examiner—Mark L. Berch
Attorney, Agent, or Firm—Arent Fox Kintner Plotkin & Kahn

[57] ABSTRACT

A process for preparing a 2-isocephem derivative characterized in that a thioacetic acid derivative which itself is basic or a mixture of a base and a thioacetic acid derivative is caused to act on a 2-azetidinyl-3,4-dihalogeno-2-butenoic acid compound represented by the general formula (1) in a water-containing organic solvent to obtain a 3-halomethyl-2-isocephem derivative represented by the general formula (2), and a process for preparing a 2-oxaisocephem derivative characterized in that a base is caused to act on a 2-azetidinyl-3,4-dihalogeno-2-butenoic acid compound represented by the general formula (1) in a water-containing organic solvent to obtain a 3-halomethyl-2-oxaisocephem derivative represented by the general formula (3)

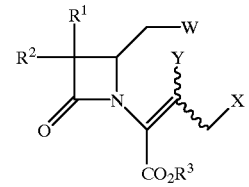

(1)

wherein $R^1$ is a hydrogen atom, amino or protected amino, $R^2$ is a hydrogen atom or lower alkoxyl, $R^1$ and $R^2$, when taken together, form a cyclic amino protecting group, $R^3$ is a hydrogen atom or carboxylic acid protecting group, W is a leaving group, and X and Y are the same or different and are each a halogen atom.

2 Claims, No Drawings

PROCESS FOR PREPARING 2-ISOCEPHEM DERIVATIVES

This is a division of application Ser. No. 08/732,446 filed Nov. 6, 1996, which is a 371 of PCT/JP96/00538 filed Mar. 6, 1996, now U.S. Pat. No. 5,688,942.

TECHNICAL FIELD

The present invention relates to a process for preparing 2-isocephem derivatives or 2-oxaisocephem derivatives. More particularly, the invention relates to a process for preparing 3-halomethyl-2-isocephem derivatives or 3-halomethyl-2-oxaisocephem derivatives useful as intermediates for introducing various functional groups into the 3-position methyl group of 2-isocephem derivatives or 2-oxaisocephem derivatives which are cephalosporin antibiotics of the unnatural type.

BACKGROUND ART

The antibacterial activities of 2-isocephem derivatives and 2-oxaisocephem derivatives are widely known [JP-A-211283/1988, J. Med. Chem., 31, 1190 (1988)]. Especially, 3-halomethyl derivatives thereof are important intermediates for preparing 3-alkenyl-2-isocephem derivatives and 2-oxaisocephem derivatives (JP-A-253008/1988, JP-A-31285/1991) which are nonnatural-type cephalosporin antibiotics, whereas reports have merely been made on several production examples of such derivatives up to date.

However, the production processes reported each have some problems, so that it has been desired to develop new production processes. For example, the processes have the following problems.

(1) The process disclosed in JP-B-32317/1986 and Can. J. Chem., Vol. 56, 1335 (1978) comprises treating a 2-azetidinyl-3,4-dihalogeno-2-butenoic acid compound with a base derived from carboxylic acid having pKa of 3.5 to 5.5 to obtain 3-acyloxymethyl-2-oxaisocephem derivative by ring closure, hydrolyzing the derivative to prepare a 3-hydroxymethyl-2-oxaisocephem derivative and treating the resulting derivative with a phosphorus halide to prepare a 3-halomethyl-2-oxaisocephem derivative as represented by the following reaction formula-1. The disclosed process results in a low yield, requires many reaction steps and uses a phosphorus compound having environmental problems such as a stringent waste water regulation.

(Reaction formula-1)

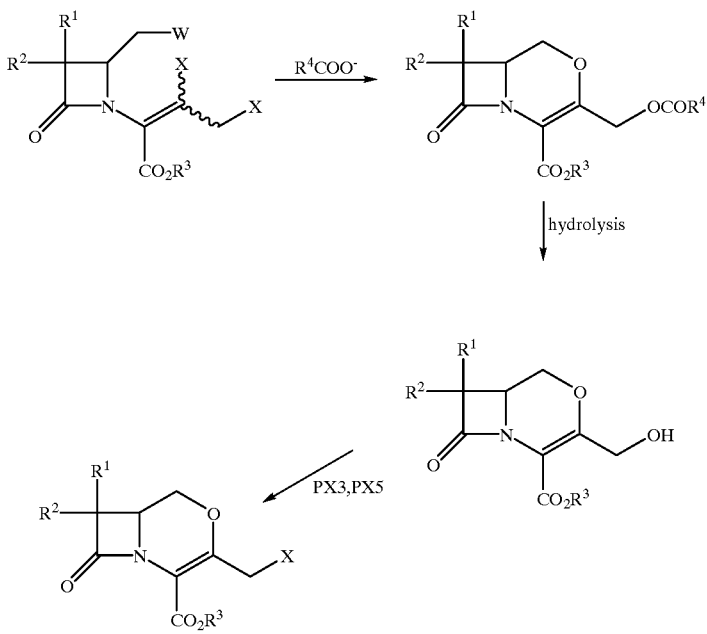

(2) The process disclosed in J-A-31285/1991 and J. Med. Chem., 31, 1190 (1988) wherein an azetidinone derivative having hydroxymethyl at the 4-position is tert-butyldimethylsilylated and then enolized with lithiumbistrimethylsilylacetamide, followed by a reaction with halogenated acetyl chloride and then by MITSUNOBU reaction (dehydration condensation reaction using an azodicarboxylic acid ester and triphenylphosphine) for ring closure uses expensive reagents, requires a cryogenic temperature, includes many steps and is therefore industrially infeasible.

(Reaction formula-2)

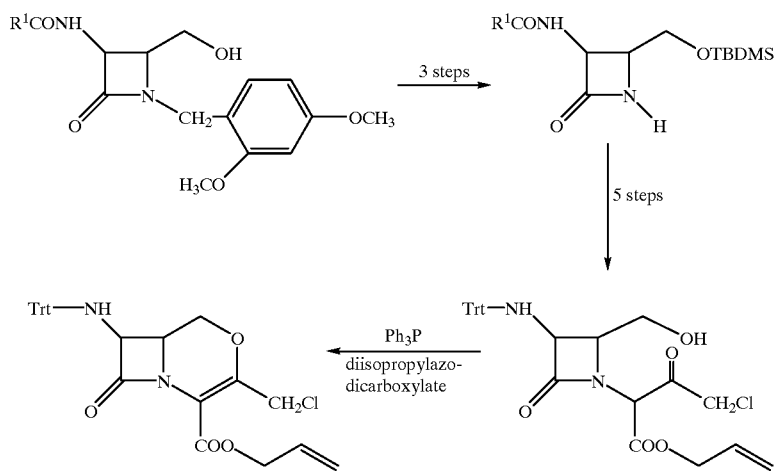

Thus, processes still remain to be developed which are free of all the problems about economy, yield, safety, work environment, etc.

An object of the present invention is to provide a novel cephem derivative production process for preparing a 3-halomethyl- 2-isocephem derivative or 3-halomethyl-2-oxaisocephem derivative by a single step from a 2-azetidinyl-3,4-dihalogeno-2-butenoic acid compound represented by the general formula (1) and easily available, effectively utilizing the halogen atom at the 4-position.

DISCLOSURE OF THE INVENTION

The present invention provides a process for preparing a 2-isocephem derivative characterized in that a thioacetic acid derivative which itself is basic or a mixture of a base and a thioacetic acid derivative is caused to act on a 2-azetidinyl-3,4-dihalogeno-2-butenoic acid compound represented by the general formula (1) in a water-containing organic solvent to obtain a 3-halomethyl-2-isocephem derivative represented by-the general formula (2), and a process for preparing a 2-oxaisocephem derivative characterized in that a base is caused to act on a 2-azetidinyl-3,4-dihalogeno-2-butenoic acid compound represented by the general formula (1) in a water-containing organic solvent to obtain a 3-halomethyl-2-oxaisocephem derivative represented by the general formula (3)

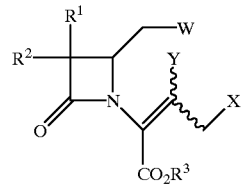

wherein $R^1$ is a hydrogen atom, amino or protected amino, $R^2$ is a hydrogen atom or lower alkoxyl, $R^1$ and $R^2$, when taken together, form a cyclic amino protecting group, $R^3$ is a hydrogen atom or carboxylic acid protecting group, W is a leaving group, and X and Y are the same or different and are each a halogen atom

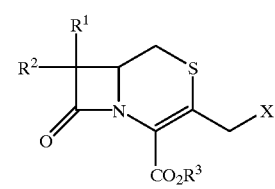

wherein $R^1$, $R^2$, $R^3$ and X are the same as above,

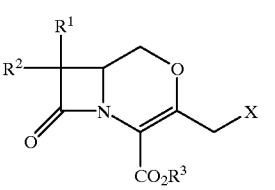

wherein $R^1$, $R^{2,}$ R and X are the same as above.

More specifically, in solving the foregoing problems of the known production processes to provide a process for preparing 3-halomethyl-2-isocephem derivatives and 3-halomethyl 2-oxaisocephem derivatives, we have found that the above-mentioned 2-azetidinyl-3,4-dihalogeno-2- butenoic acid compound, serving as a starting material, can be converted by ring closure to a 3-halomethyl-2-isocephem derivative or 3-halomethyl-2-oxaisocephem derivative which is a usual cephem antibiotic intermediate, by utilizing the difference in reactivity between the halogen atoms at the vinyl position and allyl position and the pKa value of the base to be used, as suitably combined with the difference, and effecting the conversion of the starting material through a single step with the halogen atom allowed to remain at the allyl position, and that not only the 3-halomethyl-2-oxaisocephem derivative but also the 3-halomethyl-2-isocephem derivative can be prepared from the same material by selectively using a mere base, acylthiolate derivative which itself is basic or a mixture of base and acylthiolate, in a water-containing organic solvent. These entirely novel findings have matured to the present invention.

Examples of groups mentioned herein are as follows.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10–72).

Further, also are included groups of the formula (A)

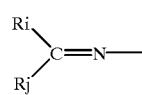

(A)

wherein Ri and Rj are same or different and each a hydrogen atom, aliphatic or aromatic hydrocarbon group or heterocyclic hydrocarbon group, or may bond together to form a cyclic group.

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

The above $R^1$ and $R^2$, when taken together, may form a cyclic amino protecting group. Exemples thereof are imido groups such as phthalimido and nitrophthalimido group.

Exemplary of the carboxylic acid protecting group represented by $R^3$ are allyl, benzyl, p-methoxybenzyl, p-nitrobenzyl, diphenylmethyl, trichloromethyl, tert-butyl, and those disclosed in the literature, Chap. 5 (pp. 152~192).

Examples of the leaving groups represented by W are halogen atoms (e.g., fluorine, chlorine, bromine and iodine), fluorosulfonyloxy, straight-chain or branched-chain $C_{1-4}$ alkylsulfonyloxy groups (e.g., methanesulfonyloxy, trifluoromethanesulfonyloxy and the like), and arylsulfonyloxy groups (e.g., benzenesulfonyloxy, toluenesulfonyloxy and the like) which may have a substituent. The most preferable is a group selected from among halogen atoms, methanesulfonyloxy, trifluoromethanesulfonyloxy and toluenesulfonyloxy. The leaving group may have 1 to 5, preferably 1 to 3, substituents. Examples of such substituents are straight-chain or branched chain hydrocarbon groups, halogen atoms including fluorine, chloride and bromine, etc.

The starting material of the invention, i.e., 2-azetidinyl-3,4-dihalogeno-2-butenoic acid compound represented by the formula (1), can be prepared, for example, by the following process.

A cupric (II) halide and a metal halide are caused to act on the allenyl group of the allenyl β-lactam compound represented by the formula (4) in a suitable solvent, whereby the compound (4) can be converted to 2-azetidinyl-3,4-dihalogeno-2-butenoic acid compound represented by the formula (1).

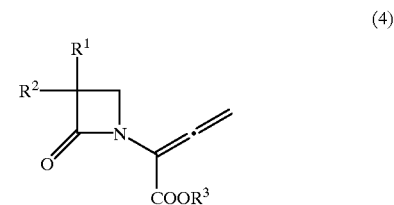

(4)

wherein $R^1$, $R^2$, $R^3$ and W are the same as above.

Examples of useful cupric (II) halides include cupric (II) chloride, cupric (II) bromide and cupric (II) iodide. While various metal salts are usable as metal halides, preferable to use are halogen salts of alkali metals and alkaline-earth metals. Examples of such salts include lithium chloride, lithium bromide, lithium iodide, calcium chloride, calcium bromide, calcium iodide, barium chloride, barium bromide, barium iodide, strontium chloride, strontium bromide, strontium iodide and the like. The cupric (II) halide is used usually in an amount of 1 to 10 equivalents relative to the allenyl β-lactam compound of the formula (1). When required, it is desirable to use an additional amount of the halide until the β-lactam compound of the formula (1) disappears. The metal halide is used usually in an amount of 1 to 10 equivalents relative to the allenyl β-lactam compound of the formula (1). When required, it is desirable to use an additional amount of the halide until the allenyl β-lactam compound of the formula (1) disappears. Although the proportion of the metal halide to be used varies with the valence and kind of metal halide, it is desirable to use the metal halide in 0.3 to 20 times, usually 0.3 to 3 times, the amount of the cupric (II) halide in molar ratio.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents are used in an amount of about 10 to about 200 liters, preferably about 20 to about 100 liters, per kilogram of the compound of the formula (1).

The reaction is conducted usually at −78° C. to 60° C., preferably −20° C. to 30° C. The reaction can be conducted, as required, in a sealed vessel, or at an atmosphere of an inert gas such as nitrogen gas. The resulting 2-azetidinyl-3,4-dihalogeno-2-butenoic acid compound of the formula (1) can be isolated by the usual purification method but is usable as prepared for the next reaction.

A thioacetic acid derivative which itself is basic, or a mixture of a base and thioacetic acid derivative, or a base is cause to act on the resulting 2-azetidinyl-3,4-dihalogeno-2-butenoic acid compound of the formula (1) in a water-containing organic solvent for ring closure, whereby the acid compound can be converted to a 3-halomethyl-2-isocephem derivative of the formula (2) or a 3-halomethyl-2-oxaisocephem derivative of the formula (3).

The thioacetic acid derivative which per se is basic for use in the present invention is a basic acylthiolate derivative, such as potassium thioacetate, sodium thioacetate or ammonium thioacetate, which is derived from carboxylic acid having a pKa of 3.5 to 5.5. The acylthiolate derivative for use with a base is, for example, thioacetic acid, thiobutyric acid, thiovaleric acid or like mercaptocarboxylic acid derivative which is 3.5 to 5.5 in pKa. These thioacetic acid derivative which per-se are basic and the thioacetic acid derivatives for use with a base are used usually in an amount of 1 to 10 equivalents, preferably 1 to 2 equivalents, relative to the 2-azetidinyl-3,4-dihalogeno-2-butenoic acid derivative of the formula (1). Useful bases, as well as these thioacetic acid derivatives for use with the base, are used singly or as a mixture of at least two of them.

Examples of bases for use in the present reaction include alkali metal hydroxides such as sodium hydroxide and potassium hydroxide, alkaline earth metal hydroxides such as calcium hydroxide and barium hydroxide, alkali metal carbonates such as sodium carbonate and potassium carbonate, alkaline earth metal carbonates such as calcium carbonate and barium carbonate, alkali metal bicarbonates such as sodium hydrogencarbonate and potassium hydrogencarbonate, alkaline earth metal bicarbonates such as calcium hydrogencarbonate and barium hydrogencarbonate, sodium hydride, bases derived from carboxylic acid having a pKa of 3.5 to 5.5 such as sodium acetate, potassium acetate and ammonium acetate, N,N,N-tri lower alkylamines such as trimethylamine, dimethylethylamine, triethylamine and diisopropylethylamine, N-lower alkylazacycloalkanes such as N-methylpiperidine and N-ethylpiperidine, N-phenyl lower alkyl-N,N-di lower alkylamine such as N-benzyl-N,N-diethylamine and N-benzyl-N,N-diethylamine, N,N-dialkyl aromatic amines such as N,N-dimethylaniline, nitrogen-containing aromatic amines such as pyridine, bicyclic amines such as diazabicycloundecene and diazabicyclononene, and mixtures of such bases. These bases are used usually in an amount of 0.1 to 10 equivalents, preferably 1 to 2 equivalents, based on the 2-azetidinyl-3,4-dihalogeno-2-butenoic acid compound of the formula (1). Such bases are used singly or in the form of a mixture of at least two of them.

Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. Among these solvents preferable is a polar solvent such as tetrahydrofuran and dimethylsulfoxide. The solvent is used as admixed with water or in the form of a two-layer system of water and the solvent. At this time, the water is used in an amount of 1 to 100 equivalents, more preferably 1 to 2 equivalents, based on the 2-azetidinyl-3,4-dihalogeno-2-butenoic acid compound of the formula (1). It is desirable to use usually about 10 to about 200 liters, preferably about 20 to 100 liters, of the solvent per kilogram of the compound of the formula (1). The reaction temperature is not critical and may conveniently be room temperature.

When required, the present reaction can be carried out in a closed container or in an inert gas, for example, in nitrogen gas. The resulting 3-halomethyl-2-isocephem derivative of the formula (2) or 3-halomethyl-2-oxaisocephem derivative of the formula (3) can be readily isolated by a usual isolation procedure.

BEST MODE OF CARRYING OUT THE INVENTION

With reference to reference examples and examples, a detailed description will be given below of the novel cephem derivative production process of the invention for preparing 3-halomethyl-2-isocephem derivative or 3-halomethyl-2-oxaisocephem derivative from a 2-azetidinyl-3,4-dihalogeno-3,4-butenoic acid compound by a single step effectively utilizing the halogen atom at the 4-position, whereas the invention is not limited only to these reference examples and examples. Incidentally, Ph stands for $C_6H_5-$.

REFERENCE EXAMPLE 1

A 559 mg quantity of compound of the formula (4a) ($R^1$=phthalimido, $R^2$=H, W=$OSO_2CH_3$, $R^3$=$CHPh_2$) (MW 558.6, 1.00 mmole) was dissolved in 6 ml of N,N-dimethylformamide, 500 mg of cupric (II) chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silica gel column chromatography, giving compound (1a) (X=Y=Cl) (558 mg, Y. 87%). $^1$H NMR (CDCl$_3$) δ: 2.79 (s, 3H), 4.31~4.65 (m, 3H), 4.55 (d, J=12 Hz, 1H), 4.88 (d, J=12 Hz, 1H), 5.60 (d, J=6 Hz, 1H), 7.02 (s, 1H), 7.21~7.53 (m, 10H), 7.78~7.95 (m, 4H)

REFERENCE EXAMPLE 2

A 559 mg quantity of compound of the formula (4a) ($R^1$=phthalimido, $R^2$=H, W=$OSO_2CH_3$, $R^3$=$CHPh_2$) (MW 558.6, 1.00 mmole) was dissolved in 6 ml of N,N-dimethylformamide, 500 mg of cupric (II) bromide (MW 143.15, 3.5 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silicagel column chromatography, giving compound (1b) (X=Cl, Y=Br) (536 mg, Y. 78%). $^1$H NMR (CDCl$_3$) δ: 2.78 (s, 1.5H), 2.80 (s, 1.5H), 4.13~4.72 (m, 3.5H), 4.58 (d, J=12 Hz, 0.5H); 4.88 (d, J=12 Hz, 0.5H), 5.09 (d, J=12 Hz, 0.5H), 5.60 (d, J=6 Hz, 1H), 7.05 (s, 0.5H), 7.06 (s, 0.5H), 7.23~7.49 (m, 10H), 7.85~7.98 (m, 4H)

REFERENCE EXAMPLE 3

A 559 mg quantity of compound of the formula (4a) ($R^1$=phthalimido, $R^2$=H, W=$OSO_2CH_3$, $R^3$=$CHPh_2$) (MW 558.6, 1.00 mmole) was dissolved in 6 ml of N,N-dimethylformamide, 500 mg of cupric (II) chloride (MW 99.0, 5.0 mmoles) and 500 mg of calcium bromide (MW 199.9, 2.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silica gel column chromatography, giving compound (1c) (X=Br, Y=Cl) (550 mg, Y. 81%). $^1$H NMR (CDCl$_3$) δ: 2.79 (s, 1.5H), 2.81 (s, 1.5H), 4.15~4.73 (m, 3.5H), 4.59 (d, J=12 Hz, 0.5H), 4.90 (d, J=12 Hz, 0.5H), 5.08 (d, J=12 Hz, 0.5H), 5.62 (d, J=6 Hz, 1H), 7.07 (s, 0.5H), 7.09 (s, 0.5H), 7.25~7.50 (m, 10H), 7.88~7.99 (m, 4H)

REFERENCE EXAMPLE 4

A 559 mg quantity of compound of the formula (4a) ($R_1$=phthalimido, $R_2$=H, W=$OSO_2CH_3$, $R^3$=$CHPh_2$) (MW 558.6, 1.00 mmole) was dissolved in 6 ml of N,N-dimethylformamide, 500 mg of cupric (II) chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silica gel column chromatography, giving compound (1d) (X=Y=Br) (634 mg, Y. 85%). $^1$H NMR (CDCl$_3$) δ: 2.79 (s, 3H), 4.31~4.65 (m, 3H), 4.55 (d, J=12 Hz, 1H), 4.88 (d, J=12 Hz, 1H), 5.60 (d, J=6 Hz, 1H), 7.02 (s, 1H), 7.21~7.53 (m, 10H), 7.78~7.95 (m, 4H)

REFERENCE EXAMPLE 5

A 603 mg quantity of compound of the formula (4b) ($R^1$=4-nitrophthalimido, $R^2$=H, W=$OSO_2CH_3$, $R^3$=$CHPh_2$) (MW 603.6, 1.00 mmole) was dissolved in 6 ml of N,N-dimethylformamide, 500 mg of cupric (II) chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silica gel column chromatography, giving compound (1e) (X=Y=Cl) (377 mg, Y. 55%). $^1$H NMR (CDCl$_3$) δ: 2.78 (s, 1.5H), 2.80 (s, 1.5H), 4.22~4.74 (m, 4H), 4.84 (d, J=12 Hz, 0.5H), 5.05 (d, J=12 Hz, 0.5H), 5.61 (d, J=6 Hz, 1H), 7.03 (s, 0.5H), 7.06 (s, 0.5H), 7.21~7.55 (m, 10H), 8.10 (d, J=3 Hz, 1H), 8.63 (d, J=3 Hz, 1H), 8.70 (bs, 1H)

REFERENCE EXAMPLE 6

A 513 mg quantity of compound of the formula (4b) ($R^1$=phthalimido, $R^2$=H, W=Cl, $R^3$=$CHPh_2$) (MW 512.5, 1.00 mmole) was dissolved in 6 ml of N,N-dimethylformamide, 500 mg of cupric (II) chloride (MW 99.0, 5.0 mmoles) and 500 mg of calcium chloride (MW 110.99, 4.5 mmoles) were added to the solution, and the mixture was stirred at room temperature for 1 hour. The reaction mixture was poured into 1N hydrochloric acid, followed by extraction with ethyl acetate. The extract was washed with water twice and with brine once, and then dried over anhydrous sodium sulfate. After removal of the solvent from the resulting extract in vacuo, the residue was purified by silica gel column chromatography, giving compound (1f) (X=Cl, Y=Br) (478 mg, Y. 82%). $^1$H NMR (CDCl$_3$) δ: 3.52~4.50 (m, 3.4H), 4.623 (d, J=12 Hz, 0.6H), 4.809 (d, J=12 Hz, 0.6H), 5.075 (d, J=12 Hz, 0.4H), 5.524 (d, J=6 Hz, 0.4H), 5.553 (d, J=6 Hz, 0.6H), 7.03 (s, 0.5H), 7.05 (s, 0.5H), 7.21~7.49 (m, 10H), 7.75~9.97 (m, 4H)

EXAMPLE 1

A 2 g quantity of compound of the formula (1a) (R$^1$=phthalimido, R$^2$=H, W=OSO$_2$CH$_3$, R$^3$=CHPh$_2$, X=Y=Cl) (MW 643, 3.00 mmoles) was dissolved in a solvent mixture of 20 ml of N,N-dimethylformamide and 0.4 ml of water, and the solution was cooled with an ice bath. Into the solution was added 450 mg of sodium formate (MW 68.01, 2.2 eq.), and the mixture was stirred for 1 hour with ice cooling and further stirred for 3 hours after removing the ice bath. After confirming disappearance of the starting material by liquid chromatography (LC), the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3a) (X=Cl) (1.6 g, purity 76.3%, yield 91% $^1$H NMR (CDCl$_3$) δ: 3.92~4.01 (m, 1H), 4.21~4.58 (m, 2H), 4.658 (dd, 2H, J=36 Hz, 4.5 Hz), 7.20~7.49 (m, 10H), 7.76~7.94 (m, 4H)

EXAMPLE 2

A 2 g quantity of compound of the formula (1a) (R$^1$=phthalimido, R$^2$=H, W=OSO$_2$CH$_3$, R$^3$=CHPh$_2$, X=Y=Cl) (MW 643, 3.00 mmoles) was dissolved in a solvent mixture of 20 ml of N,N-dimethylformamide and 0.4 ml of water, and the solution was cooled with an ice bath. Into the solution was added 754 mg of potassium thioacete (MW 114.2, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from diethyl ether, giving the desired compound (2a) (X=Cl) (1.51 g, purity 86.3%, yield 96%).

$^1$H NMR (CDCl$_3$) δ: 2.853 (dd, 1H, J=12 Hz, 3 Hz), 3.542 (dd, 1H, J=12 Hz, 10 Hz), 4.01~4.09 (m, 1H), 4.365 (dd, 2H, J=36 Hz, 12 Hz), 5.795 (d, 1H, J=5.0 Hz), 6.908 (S, 1H), 7.20~7.60 (m, 10H), 7.75~7.95 (m, 4H)

EXAMPLE 3

A 2 g quantity of compound of the formula (1a) (R$_1$=phthalimido, R$_2$=H, W=OSO$_2$CH$_3$, R$^3$=CHPh$_2$, X=Y=Cl) (MW 643, 3.00 mmoles) was dissolved in a solvent mixture of 20 ml of N,N-dimethylformamide and 0.4 ml of water, and the solution was cooled with an ice bath. Into the solution was added 540 mg of sodium acetate (MW 82.03, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3a) (X=Cl) (1.44 g, purity 80.6%, yield 87%). $^1$H NMR (CDCl$_3$) δ: 3.92~4.01 (m, 1H), 4.21~4.58 (m, 2H) 4.658 (dd, 2H, J=36 Hz, 4.5 Hz), 7.20~7.49 (m, 10H), 7.76~7.94 (m, 4H)

EXAMPLE 4

A 2.2 g quantity of compound of the formula (1d) (R$^1$=phthalimido, R$^2$=H, W=OSO$_2$CH$_3$, R$^3$=CHPh$_2$, X=Y=Br) (MW 734, 3.00 mmoles) was dissolved in a solvent mixture of 20 ml of N,N-dimethylformamide and 0.4 ml of water, and the solution was cooled with an ice bath. Into the solution was added 540 mg of sodium bicarbonate (MW 84.01, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3b) (X=Br) (1.44 g, purity 80.6%, yield 87%). $^1$H NMR (CDCl$_3$) δ: 3.90~4.08 (m, 1H), 4.20~4.55 (m, 2H) 4.395 (dd, 2H, J=45 Hz, 4.8 Hz), 5.942 (d, 1H, J=4.4 Hz), 6.951 (S, 1H), 7.20~7.62 (m, 10H), 7.76~7.95 (m, 4H)

EXAMPLE 5

A 2.1 g quantity of compound of the formula (1a) (R$^1$=4-nitrophthalimido, R$^2$=H, W=OSO$_2$CH$_3$, R$^3$=CHPh$_2$, X=Y=Cl) (MW 688, 3.00 mmoles) was dissolved in a solvent mixture of 20 ml of N,N-dimethylformamide and 0.4 ml of water, and the solution was cooled with an ice bath. Into the solution was added 450 mg of sodium formate (MW 68.01, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3c) (R=4-nitrophthalimide, X=Cl) (1.72 g, purity 77.8%, yield 95%).

$^1$H MR (CDCl$_3$) δ: 3.97~4.05 (m, 1H), 4.19~4.90 (m, 2H), 4.625 (dd, J=35.4 Hz, 5.5 Hz), 5.975 (d, 1H, J=4.8 Hz), 6.970 (S, 1H), 7.21~7.62 (m, 10H), 8.108 (d, 1H, 3.0 Hz), 8.668 (d, 1H, 3.0 Hz), 8.718 (S, 1H)

EXAMPLE 6

A 2.1 g quantity of compound of the formula (1b) (R$^1$=phthalimido, R$^2$=H, W=OSO$_2$CH$_3$, R$^3$=CHPh$_2$, X=Cl, Y=Br) (MW 689, 3.00 mmoles) was dissolved in a solvent mixture of 20 ml of N,N-dimethylformamide and 0.4 ml of water, and the solution was cooled with an ice bath. Into the solution was added 540 mg of sodium bicarbonate (MW 84.01, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3a) (X=Cl) (1.47 g, purity 79.1%, yield 87%).

$^1$H NMR (CDCl$_3$) δ: 3.92~4.01 (m, 1H), 4.21~4.58 (m, 2H), 4.658 (dd, 2H, J=36 Hz, 4.5 Hz), 7.20~7.49 (m, 10H), 7.76~7.94 (m, 4H)

EXAMPLE 7

A 1.8 g quantity of compound of the formula (1f) (R$^1$=phthalimido, R$^2$=H, W=Cl, R$^3$=CHPh$_2$, X=Y=Cl) (MW 688, 3.00 mmoles) was dissolved in a solvent mixture of 20 ml of N,N-dimethylformamide and 0.4 ml of water, and the solution was cooled with an ice bath. Into the solution was added 450 mg of sodium formate (MW 68.01, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from isopropyl alcohol, giving the desired compound (3a) (X=Cl) (1.41 g, purity 79.9%, yield 84%). $^1$H NMR (CDCl$_3$) δ: 3.92~4.01 (m, 1H), 4.21~4.58 (m, 2H), 4.658 (dd, 2H, J=36 Hz, 4.5 Hz), 7.20~7.49 (m, 10H), 7.76~7.94 (m, 4H)

EXAMPLE 8

A 1.8 g quantity of compound of the formula (1f) (R$^1$=phthalimido, R$_2$=H, W=Cl, R$_3$=CHPh$_2$, X=Y=Cl) (MW 583.8, 3.00 mmoles) was dissolved in a solvent mixture of 20 ml of N,N-dimethylformamide and 0.4 ml of water, and the solution was cooled with an ice bath. Into the solution was added 754 mg of potassium thioacetate (MW 114.22, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from diethyl ether, giving the desired compound (2a) (X=Cl) (1.38 g, purity 90.0%, yield 92% $^1$H NMR (CDCl$_3$) δ: 2.853 (dd, 1H, J=12 Hz, 3 Hz), 3.542 (dd, 1H, J=12 Hz, 10 Hz), 4.01~4.09 (m, 1H), 4.365 (dd, 2H, J=36 Hz, 12 Hz), 5.795 (d, 1H, J=5.0 Hz), 6.908 (S, 1H), 7.20~7.60 (m, 10H), 7.75~7.95 (m, 4H)

EXAMPLE 9

A 2 g quantity of compound of the formula (1g) (R$_1$=phthalimido, R$^2$=H, W=OSO$_2$CH$_3$, R$^3$=CH$_2$C$_6$H$_4$—NO$_2$, X=Y=Cl) (MW 643, 3.00 mmoles) was dissolved in a solvent mixture of 20 ml of N,N-dimethylformamide and 0.4 ml of water, and the solution was cooled with an ice bath. Into the solution was added 450 mg of sodium formate (MW 68.01, 2.2 eq.), and the mixture was stirred for 1 hour with ice cooling and further stirred for 3 hours after removing the ice bath. After confirming disappearance of the starting material by LC, the reaction mixture was poured into 50 ml of ethyl acetate, followed by washing with 50 ml of brine. The organic layer was dried over anhydrous magnesium sulfate and then purified by silica gel chromatography. The product was crystallized from ethyl alcohol, giving the desired compound (d) (X=Cl) (1.29 g, purity 88.8%, yield 94%). $^1$H NMR (CDCl$_3$) δ: 3.948 (dd, 1H, J=11.0 Hz, 5.0 Hz), 4.19~4.58 (m, 4H), 5.373 (dd, 2H, J=27 Hz, 5.5 Hz), 5.891 (d, 1H, J=4.8 Hz), 7.689 (d, 2H, J=3.0 Hz), 7.78~7.90 (m, 4H), 8.21 (d, 2H, J=3.0 Hz)

REFERENCE EXAMPLE 7

A 720 mg quantity of benzhydryl (6S,7S)-7-phthalimido-3-chloromethyl-8-oxo-4-oxa-1-azabicyclo[4.2.0]-oct-2-ene-carboxylate [compound (3a)] was completely dissolved in 4 ml of N,N-dimethylformamide, and the solution was cooled between 0° C. and 5° C. with an ice bath. Three (3) ml of a solution of 100% hydrazine hydrate in N,N-dimethylformamide (0.5M soln.) was added dropwise to the solution between 0° C. and 5° C., followed by heating to room temperature. After disappearance of the starting material was confirmed by liquid chromatography, 7 ml of ethanol and 3.3 ml of 1N HCl aq. were added to the reaction mixture, followed by stirring at room temperature (whereby particles were precipitated).

Two hours later, the solvent was removed to some extent, 20 ml of water and 10 ml of ether were added to the residue, and the mixture was transferred into a separatory funnel to collect an aqueous layer. The layer was cooled in an ice bath and adjusted to a pH of 8 to 9 by adding powdery sodium bicarbonate in small portions. The resulting aqueous layer was extracted with ethyl acetate, the extract was dried over anhydrous magnesium sulfate, the solvent was evaporated in vacuo, and the residue was purified by silica gel column chromatography, yielding 360 mg of the desired compound, i.e., benzhydryl (6S,7S)-7-amino-3-chloromethyl-8-oxo-4-oxa-1-azabicyclo[4.2.0]oct-2-ene-carboxylate (Y. 70%). $^1$H NMR (CDCl$_3$+D$_2$O) δ: 3.62~3.76 (m, 1H), 3.970 (dd, 1H, J=11.0 Hz, 12.0 Hz), 4.582 (dd, 2H, J=36 Hz, 12 Hz), 4.680 (dd, 1H, J=12.0 Hz, 4.0 Hz), 4.813 (d, 1H, J=5.0 Hz), 6.804 (s, 1H), 7.224~7.601 (m, 10H)

REFERENCE EXAMPLE 8 a) A 1.0 g quantity of benzhydryl (6S,7S)-7-amino-3-chloromethyl-8-oxo-4-oxa-1-azabicyclo[4.2.0]oct-2-ene-carboxylate, 0.45 ml of triethylamine and 100 ml of methylene dichloride were added to a solution, then 1.1 g of 2-(2-tritylaminothiazol-4-yl)-2-cyanomethoxyiminoacetic acid (syn isomer) was added, followed by stirring with ice cooling. After addition of 0.5 g of dicyclohexylcarbodiimide (DCC), the mixture was stirred for overnight. The resulting precipitate was filtered and washed with water, dried over anhydrous magnesium sulfate. After removing the solvent, the residue was purified by silica gel chromatography, yielding 0.91 g of benzhydryl (6S,7S)-7-{2-(2-tritylaminothiazol-4-yl)-2-cyanomethoxyiminoacetamido}-3-chloromethyl-8-oxo-4-oxa-1-azabicyclo[4.2.0]oct-2-ene-carboxylate.

b) The above-mentioned 2-aminothiazole compound was dissolved as it was in 50 ml of methylene dichloride, 0.7 g of 1,3,4-thiadiazole-2-thiol and 0.7 ml of triethylamine were added to the solution, and the mixture was stirred at room temperature for 1 hour and 30 minutes. The reaction mixture was washed with 5% aqueous solution of sodium bicarbonate once and with water twice. After removal of the solvent, 1.0 ml of anisole was added to the residue, 5 ml of trifluoroacetic acid was added dropwise to the mixture with ice cooling and the mixture was stirred for 10 minutes. Then diethyl ether was added to the reaction mixture, crystals separated out, which were filtered off, washed with diethyl ether and dried, giving 0.2 g of the desired active β-lactam antibiotic, i.e., (6S,7S)-7-(2-aminothiazol-4-yl-2-cyanomethoxyiminoacetamido)-3-{(1,3,4-thiadiazol-2-yl)-thiomethyl}-8-oxo-4-oxa-1-azabicyclo[4.2.0]oct-2-ene-carboxylate in the form of crystals. $^1$H-NMR (DMSO) δ: 3.58~4.21 (m, 2H), 4.33~4.85 (m, 1H), 4.56 (s, 2H), 5.06 (s, 2H), 5.75 (dd, 1H), 7.00 (s, 1H), 9.50 (s, 1H), 9.58 (s, 1H)

INDUSTRIAL APPLICABILITY

According to the present invention, it is possible to prepare 3-halomethyl-2-isocephem derivatives or 3-halomethyl-2-oxaisocephem derivatives by a single step from 2-azetidinyl-3,4-dihalogeno-2-butenoic acid compounds represented by the general formula (1) as a starting material, effectively utilizing the halogen atom at the 4-position of the starting material.

(2)

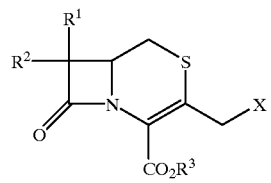

wherein $R^1$, $R^2$, $R^3$ and X are the same as above, (3)

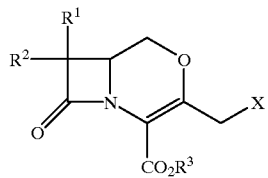

wherein $R^1$, $R^2$, $R^3$ and X are the same as above.

What is claimed is:

1. A process for preparing a 2-oxaisocephem derivative comprising reacting a base with a 2-azetidinyl-3,4-dihalogeno-2-butenoic acid compound represented by formula (1) in a water-containing organic solvent to obtain a 3-halomethyl-2-oxaisocephem derivative represented by formula (3), wherein the base is used in an amount of 0.1 to 2.2 equivalents per compound represented by formula (1), (1)

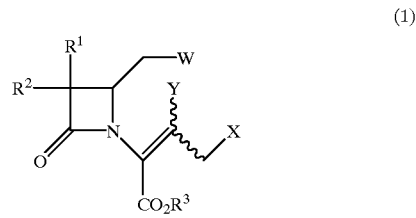

wherein $R^1$ is a hydrogen atom, amino or protected amino and $R^2$ is a hydrogen atom or lower alkoxyl, $R^3$ is a hydrogen atom or carboxylic acid protecting group, W is a leaving group, and X and Y are the same or different and are each a halogen atom, (3)

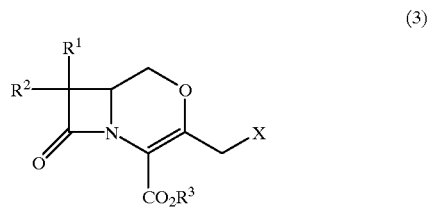

wherein $R^1$, $R^2$, $R^3$ and X are the same as above.

2. A process as defined in claim 1, wherein the base is alkali metal hydroxide, alkaline earth metal hydroxide, alkali metal carbonate, alkaline earth metal carbonate, alkali metal bicarbonate, alkaline earth metal bicarbonate, sodium hydride, sodium acetate, potassium acetate, ammonium acetate, N,N,N-tri lower alkylamine, N-lower alkylazacycloalkane, phenyl lower alkyl-di lower alkylamine, aromatic carbocycle having a dialkyl amino substituent, an aromatic heterocycle containing carbon and nitrogen atoms, diazabicyclononene or diazabicycloundecene.

* * * * *